United States Patent [19]

Scrivens

[11] 4,033,341
[45] July 5, 1977

[54] SURGICAL DRAPE HAVING IMPROVED RETAINING MEANS

[75] Inventor: George W. Scrivens, Edison, N.J.

[73] Assignee: Johnson & Johnson, New Brunswick, N.J.

[22] Filed: Mar. 3, 1976

[21] Appl. No.: 663,958

[52] U.S. Cl. .................... 128/132 D; 128/DIG. 26
[51] Int. Cl.² ......................................... A61B 19/06
[58] Field of Search ............. 128/132 D, 292, 348, 128/DIG. 26

[56] References Cited

UNITED STATES PATENTS

| | | | |
|---|---|---|---|
| 1,724,443 | 8/1929 | Wheeler | 128/132 D |
| 3,503,391 | 3/1970 | Melges | 128/132 D |
| 3,561,440 | 2/1971 | Bayer et al. | 128/132 D |
| 3,721,234 | 3/1973 | Hadtke et al. | 128/132 D |
| 3,881,474 | 5/1975 | Krzewinski | 128/132 D |

FOREIGN PATENTS OR APPLICATIONS 624,676  8/1961  Canada ..................... 128/DIG. 26

*Primary Examiner*—Lawrence W. Trapp

[57] ABSTRACT

An improved surgical drape comprising a main sheet of flexible drapable material having secured thereto a retainer member made from a flexible material and comprising a conduit through which tubing, electrical wires and the like may be threaded and thereby secured to the surface of the drape. The flexible material comprising the retainer member is selected from the group consisting of woven fabrics, non-woven fabrics, polymeric films, and a liquid absorbent material laminated to a polymeric film. The drape may also include a reinforcing panel and, in a preferred embodiment, the reinforcing panel and the retainer member are made from a single piece of material. Methods for making such drapes are also disclosed.

28 Claims, 11 Drawing Figures

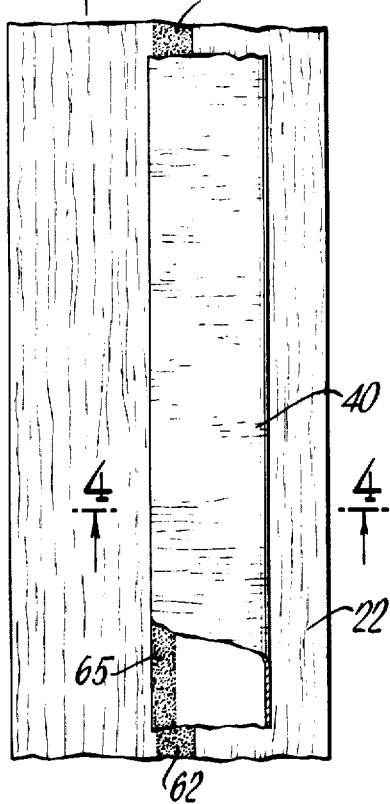
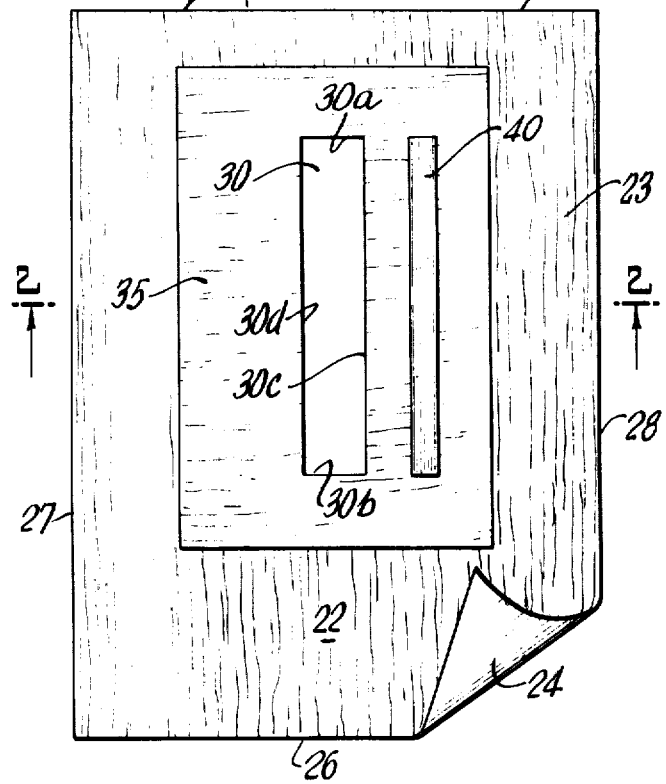
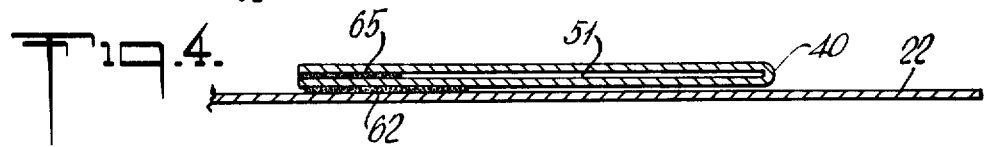
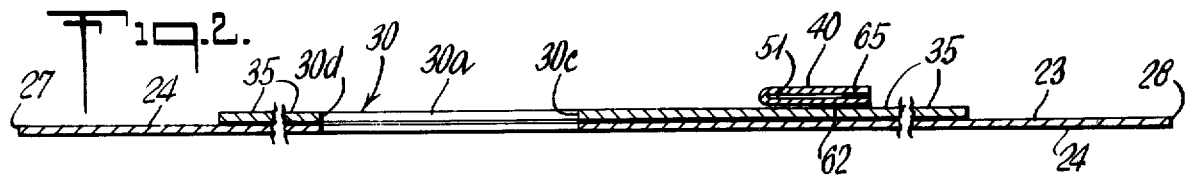
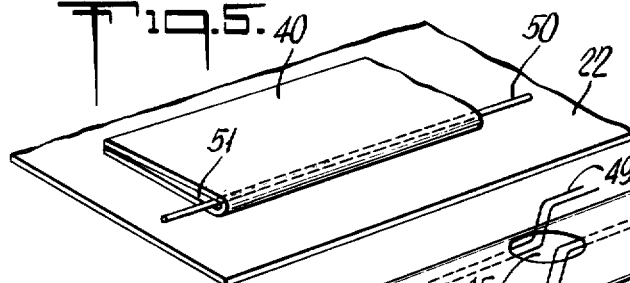
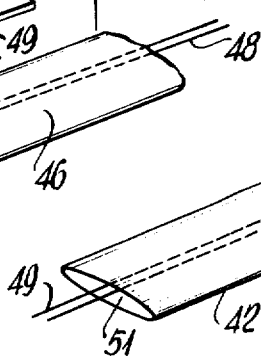
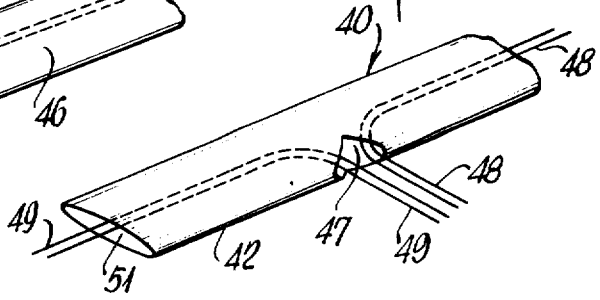

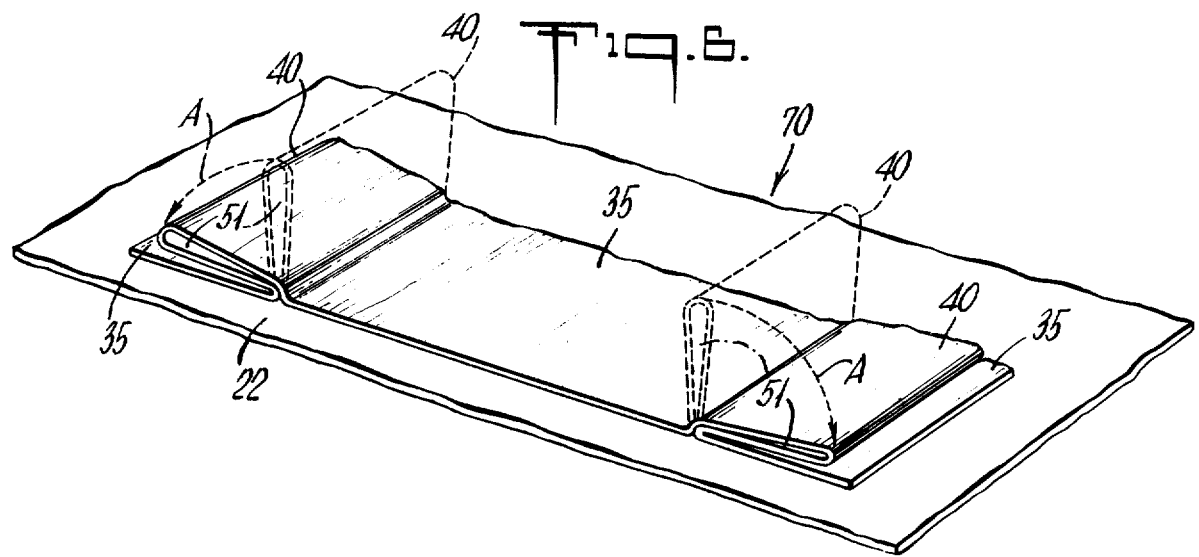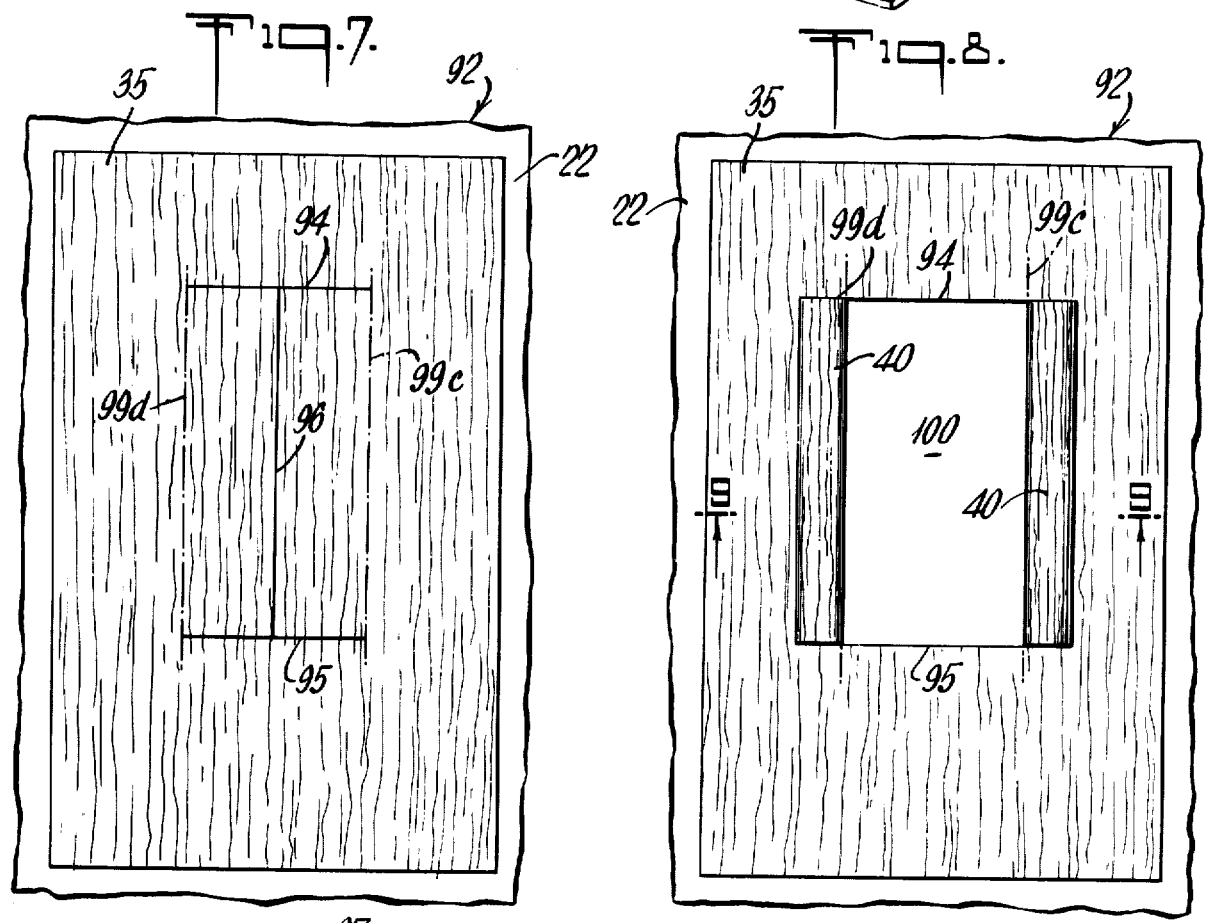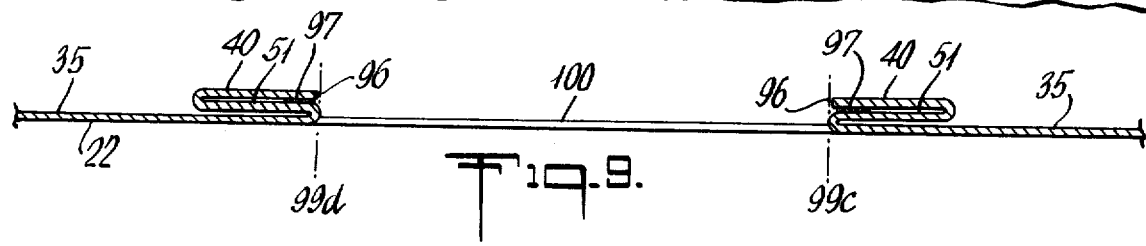

SURGICAL DRAPE HAVING IMPROVED RETAINING MEANS

BACKGROUND OF THE INVENTION

1. Field of the Invention

This invention relates to surgical drapes and the like and, more particularly, to improved disposable surgical drapes which comprise improved means for covering and securing thin elongated flexible members such as suction tubing and electrical wires on the upper surface thereof.

2. DESCRIPTION OF THE PRIOR ART

During certain types of surgical procedures, it is quite common to employ suction devices to keep the wound site free of fluid. In recent years, it has also become quite common to employ surgical diathermy and electrocautery devices during surgical procedures to control bleeding. Both the suction devices and the diathermy and cautery devices employ thin elongated flexible members, hollow suction tubing in the case of the suction devices and electrical cords or wires in the case of diathermy or cautery devices, at or near the operative site.

When the patient is covered with a surgical drape (whether a reusable linen drape or a disposable nonwoven or paper drape), the aforementioned elongated flexible members can be kept in their desired position by the use of towel clamps or towel clips.

The repeated use of towel clamps on reusable linen drapes gradually and disadvantageously results in perforation, and sometimes also tearing, of the drape. Disposable nonwoven or paper surgical drapes are structurally weaker than the linen drapes so that any use whatever of towel clamps usually results in perforation and/or tearing of the drape. In either case, such perforation or tearing is unacceptable in that paths may be thereby provided along which bacteria may migrate between the draped patient and members of the surgical team.

In accordance with the invention disclosed in U.S. Pat. No. 3,721,234 (Hadtke), a disposable surgical cover sheet comprises a main sheet having an enlarged opening therein. This opening is covered by a sheet of plastic material which is bonded to the main sheet in a bonding zone. Portions of the plastic sheet project beyond the bonding zone and may be used to retain e.g., a suction tube without risking the puncture or tearing of the cover sheet.

U.S. Pat. No. 3,881,474 (Krzewinski) discloses a surgical drape which has tabs which may be used to fasten tubing or cords in place during a surgical procedure. Each of the tabs has a flexible portion free of the body of the drape, the flexible portion having at least two openings through which a flexible member may be threaded.

SUMMARY OF THE INVENTION

A principal feature of the present invention is the provision of a surgical drape which comprises improved means for covering and securing elongated members improved means for covering and securing elongated members such as suction tubing, electric power leads and the like on the upper surface of the drape.

The drape of the present invention comprises a main sheet of flexible drapable material having an upper surface and a lower surface, the lower surface being that surface which will contact the patient's body and the upper surface being that surface which will face away from the patient's body while the drape is in use. Preferably, the drape has a reinforcing panel to add strength and abrasion resistance in the operative area thereof. Depending on the particular end use, the drape may have a more or less centrally located fenestration which may be of any desired shape or configuration.

In accordance with another aspect of the present invention, the aforementioned means for covering and securing elongated elements to the drape may be formed directly from either the main sheet itself or from the reinforcing panel of the drape, thus reducing the time needed to manufacture the drape.

If it is desired to make a fenestrated drape, then in accordance with still another aspect of the present invention, it is possible to form the covering and securing means from the material which would otherwise be cut out and discarded during formation of the fenestration.

BRIEF DESCRIPTION OF THE DRAWINGS

In the accompanying drawings:

FIG. 1 is a top plan view, with portions turned up, of one embodiment of a surgical drape in accordance with the present invention;

FIG. 2 is an enlarged cross-sectional view taken along line 2—2 of FIG. 1;

FIG. 3 is an enlarged fragmentary view, with portions cut away, showing the improved means by which elongated elements may be held in desired position on a surface of a surgical drape;

FIG. 4 is an enlarged cross-sectional view taken along line 4—4 of FIG. 3;

FIG. 5 is a fragmentary perspective showing an electric wire threaded through the aforementioned improved holding means;

FIG. 5a is a fragmentary perspective wherein the holding means includes circular opening;

FIG. 5b is a fragmentary perspective wherein the holding means includes a cut or opening in its side edge;

FIG. 6 is a fragmentary perspective view of a surgical drape in which the holding means is made from the same sheet of material which comprises the reinforcing panel of the drape;

FIG. 7 is a top plan view of a sheet of flexible drapable material prior to its conversion to a fenestrated drape comprising improved means for securing and covering elongated, flexible members;

FIG. 8 is a top plan view of the surgical drape made from the sheet material illustrated in FIG. 7; and FIG. 9 is an enlarged, schematic cross-section taken along line 9—9 of FIG. 8.

DESCRIPTION OF THE PREFERRED EMBODIMENTS

Referring now to FIGS. 1–4, there is shown a surgical drape in accordance with the present invention. Surgical drape 20 is four sided in configuration and comprises a main sheet 22 of flexible, drapable material; a fenestration 30 through which the surgeon may perform a surgical procedure; a reinforcing panel 35; and a retainer member 40 by means of which auxiliary surgical equipment in the form of elongated, more or less flexible elements, such as electrical wires, suction tubing and the like may be securely retained on the drape.

Main sheet 22, which may comprise any flexible, drapable woven, nonwoven, or plastic material, has an upper surface 23, a lower surface 24, a first end or top edge 25, a second end or bottom edge 26, and a pair of opposed side edges 27, 28. It will be understood that, in the surgical drape under discussion, lower surface 24 will contact the patient when the drape in in use, while upper surface 23 will face away from the patient. Preferably, main sheet 22 comprises a generally flexible, drapable nonwoven fabric treated to make it repellent to liquids, such as water, blood, alcohol, saline, and wound exudate, normally encountered in medical or surgical procedures.

In the embodiment illustrated in FIGS. 1–4, fenestration 30 is generally rectangular in shape and is defined by interior edges 30a, 30b, 30c, and 30d of main sheet 22. Fenestrations or openings defined by interior edges of a surgical drape are well known in the art and fenestration 30 may, according to the particular purpose for which the drape is intended, have an oval, square, circular or similar configuration. In certain cases, for example where it is desired to drape portions of the patients's body which are not immediately involved with the surgery, it may be unnecessary, or even undesirable, to have a fenestration in the drape.

Fenestration 30 is optionally surrounded on the upper surface of the drape by a reinforcing panel 35 which provides increased strength and resistance to abrasion. The reinforcing panel may comprise a second layer of the same material used for main sheet 22 or it may be a different material. Where it is desired to have a reinforcement, panel 35 preferably comprises a liquid absorbent nonwoven fabric laminated to a thin sheet of liquid impervious polymeric film. The reinforcing panel is secured to the main sheet by any convenient means, but preferably with an adhesive, so that its liquid impervious film portion is next to the upper surface of the main sheet. The liquid absorbent surface of the reinforcing panel is then exposed on the upper surface of the drape where it can quickly absorb liquid normally encountered during surgery.

As mentioned, modern surgery techniques involve the use of certain auxiliary medical or surgical equipment which include thin, elongated, more or less flexible members such as suction tubing, and electrical wires from electric cautery devices, monitoring devices, and the like. It is necessary that such tubing and wires be readily available near the operative site. At the same time, however, these items must be arranged and secured so that they do not interfere with the surgical procedure and so that they will not inadvertently move from their desired place on the drape.

In accordance with the present invention there is provided a retainer member by means of which the aforementioned flexible elements may be retained in the desired position on the drape when the latter is in use. Advantgeously, my retainer member is such that flexible elements like suction tubing, in addition to being retained on and secured to the surface of the drape, are also covered in the regions adjacent the operative site. This is in contrast to prior art devices wherein substantial or almost entire portions of a flexible element like tubing were left exposed on the surface of the drape in the area of the operative region after being threaded through adjacent holes in a tab or after being attached, by surgical clips or forceps, to relatively small, tab-like elements or projections. Thus, with the retainer member of the present invention, it is much less likely that elongated elements retained on the drape near the operative site will interfere with or disrupt the surgical procedure at hand.

Retainer member 40 comprises a more or less flat, elongated, open-ended envelope or container comprising a flexible, drapable material such as a plastic or a woven or nonwoven fabric. Retainer member 40 is open at the opposed ends thereof and, as can be seen in FIGS. 2, 3, 4, comprises a conduit or channel 51 through which electrical wires or tubing may be threaded and thereby enclosed. As mentioned, the retainer member, which in the form it assumes prior to actual use is perhaps best thought of as a flattened tube of material reminiscent of a coin wrapper prior to its use, is open at both ends thereof. In use, an electric wire 50, or similar element, is threaded through the retainer member, entering at one end and exiting at the other. This is illustrated in FIG. 5, where electrical wire 50 is seen threaded through conduit 51 of retainer member 40.

If it is desired to make a non-reinforced surgical drape, then retainer member 40 is preferably made from the same material as main sheet 22. If it is desired to make a reinforced surgical drape like the one illustrated in FIG. 1, then it is preferable, although not necessary, to make retainer member 40 from the same kind of material as used for reinforcing panel 35.

Modifications of retainer member 40 are shown in FIGS. 5a and 5b. In FIG. 5a, the material comprising member 40 has been formed into a generally flattened, somewhat elliptical cross-section and an opening 45 has been cut into one of the side walls 46 thereof. With this arrangement a first element 49 can be threaded through one end of member 40 and out opening 45 and a second element 48 may be threaded through opening 45 and out the other end of the member. In FIG. 5b, a V-shaped opening 47 has been cut into one of the more or less flattened side edges 42 of retainer member 40. A possible arrangement of flexible elements 48 and 49 is illustrated in FIG. 5b. It will be recognized that a plurality of openings may be provided in member 40; that the openings themselves may assume a variety of configurations; and that the openings may be placed in various locations (e.g., in a side wall or in a flattened edge) in member 40. If it becomes necessary during a surgical procedure a member of the surgical team could cut an additional opening(s) into the retainer member at any desired position to accommodate additional flexible elements.

Retainer member 40 can be easily assembled by selecting two generally rectangular, substantially equally sized pieces of suitable material, e.g., a nonwoven fabric, each having a top edge, a bottom edge and a pair of opposed side edges. The length and width of the two pieces of material are selected to correspond to the length and width desired for retainer member 40. The pieces of material are laid one on top of the other such that their respective side, top, and bottom edges are in alignment. The pieces of material are then joined, e.g., by stitching or with adhesive, along their aligned side edges to form the retainer member. The aligned top edges and the aligned bottom edges are, of course, left unsecured to each other to provide the channel or conduit through which the flexible elements may be threaded and thereby enclosed.

Alternatively, retainer member 40 may be formed by selecting a flat piece of suitable material whose length corresponds to the length desired for the retainer member and whose width is slightly more than twice the width desired in the retainer member. This piece of material is then folded in half around a longitudinal fold line so that the side edges of the flat sheet are in substantial alignment. As shown in FIG. 3, a narrow strip of adhesive 65 is applied to the folded piece of material adjacent the aligned side edges to form the retainer means.

Retainer member 40 is then secured by adhesive 62 to the upper surface of the surgical drape. The retainer member can be attached at any desired location on the drape. In the preferred embodiment under discussion, and as illustrated in FIG. 1, retainer member 40 runs lengthwise of drape 20 and is placed a short distance, e.g., about 3 to about 5 inches from edge 30c of the fenestration. Also it is preferred, although not necessary, that retainer member 40 be as long as the edge (in this case, 30c) of the fenestration adjacent which it has been placed. This arrangement provides substantial coverage, along the entire length of the edge of the fenestration, of flexible elements which are threaded through the retainer member. Thus, the size of retainer member 40, and its location on the upper surface of the drape, insure that any flexible elements threaded therethrough will be kept relatively near the operative site and also substantially covered in that area of the drape.

In accordance with another aspect of the present invention, there is provided a reinforced surgical drape, which optionally may have a fenestration, in which retainer means 40 and reinforcing panel 35 are formed from the same piece of material. This reduces trim waste and saves time in the manufacture of the drape.

Referring now to FIG. 6, there is shown in fragmentary view a reinforced surgical drape 70 wherein retainer members 40 and reinforcing panel 35 comprise a single sheet of flexible drapable material. Preferably this sheet of material has a liquid absorbent upper surface and a liquid impervious lower surface. The first step in making drape 70 is to cut a piece of the desired reinforcing material to a suitable length and width. It is then a simple matter to provide looped portions in this reinforcing material to form the retainer member. Referring to FIG. 6, it will be noticed that two retainer members 40 have been provided, and it will be understood that in some instances only one such member may be desired or needed. Retainer members formed in this way will have a length corresponding to the length of the reinforcing material. After the reinforcing material is looped to form the retainer members, adhesive may, if desired, be placed at the base of the looped portions along the length of the retainer members. Thereafter the liquid impervious lower surface of the looped reinforcing material is secured, preferably with adhesive (not illustrated in FIG. 6) to the upper surface of main sheet 22, thus leaving its absorbent surface exposed on the upper surface of the drape. It will be appreciated that adhesive need not necessarily be placed at the base of the looped portions because when the one-piece reinforcing panel/retainer member is later secured to the main sheet 22 of the drape, the looped portions will automatically retain their configuration. As indicated by arrow A in FIG. 6, the retainer members 40 can be easily folded downwardly from their upstanding position to lie flat on the upper surface of the drape.

In accordance with still another aspect of the present invention, there is provided a fenestrated surgical drape in which the material which would otherwise be cut away and discarded durin the formation of the fenestration is used to form one or more retainer members which lie immediately adjacent the edges of the fenestration.

This aspect of the invention will be described with reference to FIGS. 7–9. As shown in FIG. 7, the flexible, drapable material 92 from which the drape will be made, preferably comprises a main sheet 22 to which has been secured a reinforcing panel 35. It will be recognized that in certain cases it may be desired to omit the reinforcing panel comprising material 92. Two horizontal lines 94, 95, are marked on material 92. The length of these lines should correspond approximately to the width which is desired in the fenestration in the drape. Line 96 is marked on sheet 92, preferably so as to bisect lines 94, 95. The length of line 96, i.e., the distance between lines 94 and 95, should correspond substantially to the length of the fenestration in the drape. Sheet 92 is then cut along lines 94, 95, and 96 to form two flaps of material which are "hinged" or foldable around dot and dash lines 99c and 99d, respectively. Each of the flaps is then folded in half backwardly (i.e., in a direction so that the under surface of material 92 is brought into contact with itself) and secured in this folded configuration with a layer of adhesive 97 (See FIG. 9) to form retainer members 40. Each retainer member is then folded along dotted lines 99c, 99d so that it lies on the upper surface of material 92. The foregoing steps provide a fenestration 100 whose length corresponds to the length of line 96 and whose width is equal to the length of lines 94, 95. Retainer members 40 then lie immediately adjacent the longitudinal edges of fenestration 30. It will be observed that lines 94 and 95 (after material 92 are analogous to interior edges 30a and 30b in FIG. 1 and has been cut) define the upper and lower edges, respectively, of fenestration 100. Similarly, dotted lines 99c and 99d are analogous to side edges 30c, 30d in FIG. 1 and define the opposed side edges of fenestration 100.

It will be understood that many variations of the arrangement illustrated in FIGS. 7–9 will occur to those skilled in the art. For example, the relative sizes of the two members 40 may be changed by moving line 96. If line 96 in FIG. 7 be moved to the right, then retainer member 40 adjacent line 99d would be wider than retainer member 40 adjacent line 99c. Line 96 could be moved to coincide with, for example, line 99c in FIG. 7. The drape would then have one retainer member 40 which would be adjacent line 99d and whose width would correspond substantially to the width of fenestration 100. It will be recognized that retainer members 40 be located to run parallel to the sides of the drape (as shown in FIG. 7–9) or to the top and bottom edges of the drape.

Regarding drape 20 in FIGS. 1–4, it will be recognized that retainer member 40 can be secured to the drape at any number of locations and, in some instances, two or even more retainer members can be employed.

Retainer member(s) 40 should, of course, be "flattened" against the surface of the drape (i.e., into the position illustrated in FIG. 2, 4, and 9) prior to the usual folding of the drape in the longitudinal direction. The folded drape may be suitably packaged and sterilized in its packaged condition by the manufacturer, thus obviating the need for sterilization by the hospital prior to use.

While the invention has been described in connection with its preferred embodiments, it will be understood that it is not intended to limit the invention to those embodiments. On the contrary, it is intended to cover all alternatives, modifications and equivalents as may be included within the spirit and scope of the invention as defined by the appended claims.

I claim:

1. A surgical drape comprising a main sheet of flexible, drapable material, said main sheet having an upper surface, a lower surface, a top edge, a bottom edge, and a pair of opposed side edges, said main sheet having secured to its upper surface along a single line of attachment at least one retainer member made from a generally flexible material and comprising an elongated, open-ended conduit through which flexible elements such as suction tubing and the like may be threaded and thereby retained in desired position on the drape.

2. A surgical drape according to claim 1 wherein said retainer member comprises a material selected from the group consisting of a plastic film, a woven fabric, a non-woven fabric, and a liquid absorbent material laminated to a polymeric film.

3. A surgical drape according to claim 2 wherein said main sheet further includes a reinforcing panel secured to said main sheet.

4. A surgical drape according to claim 3 wherein said reinforcing panel and said retainer member are made from the same piece of material.

5. A surgical drape according to claim 4 wherein said piece of material comprises a liquid absorbent material laminated to a polymeric film.

6. A surgical drape according to claim 2 wherein said main sheet has a fenestration therein.

7. A surgical drape according to claim 2 wherein said main sheet further comprises a reinforcing panel and a fenestration, said fenestration being located within the outer edges of said reinforcing panel.

8. A surgical drape according to claim 7 wherein said retainer member lies between an edge of said fenestration and an edge of said reinforcing panel.

9. A surgical drape according to claim 1 wherein said main sheet comprises a nonwoven fabric and said retainer member comprises a liquid absorbent material laminated to a polymeric film.

10. A method for making a fenestrated surgical drape comprising:
a. providing a main sheet of flexible drapable material having an upper surface, a lower surface, and a pair of opposed edges;
b. marking the first and second lines on said main sheet inwardly of said opposed edges;
c. marking on said main sheet a third line which joins said first and said second lines;
d. cutting said main sheet along said first, said second, and said third lines to form at least one flap having an upper surface and a lower surface;
e. folding said one flap so that one of said upper and lower surfaces comes into contact with itself; and
f. securing said flap in said folded configuration.

11. A method according to claim 10 wherein said main sheet is further provided with a reinforcing panel.

12. A method according to claim 11 wherein said lines are marked on said reinforcing panel.

13. A method according to claim 12 wherein said first and second lines are generally parallel to each other.

14. A method according to claim 13 wherein said third line is generally perpendicular to said first and said second lines.

15. A method according to claim 14 wherein said third line substantially bisects said first and said second lines.

16. A method for making a reinforced, fenestrated surgical drape, said drape having an upper surface, a lower surface, and at least one retainer member comprising a conduit through which flexible elements such as suction tubing and electrical wires may be threaded to secure them to said drape, said method comprising:
a. providing a main sheet of flexible drapable material having an upper surface, a lower surface, and a pair of opposed edges;
b. providing a reinforcing panel of flexible, drapable material;
c. securing said reinforcing panel to the upper surface of said main sheet to form a reinforced main sheet;
d. marking first and second lines on said reinforced main sheet; said first line being generally parallel to said second line;
e. marking on said reinforced main sheet a third line which joins joins and bisects said first and said second lines;
f. cutting through said reinforced main sheet along said first, said second, and said third lines to form first and second flaps, said first and second flaps each having an upper surface and a lower surface and being substantially equal in size;
g. folding each of said flaps in half backwardly upon itself; and
h. securing each of said flaps in its folded configuration whereby there is formed a retainer member comprising a conduit through which flexible members such as suction tubing and electrical wires may be threaded and secured to the drape.

17. A method according to claim 16 wherein said secured, folded flaps are folded to overlie the upper surface of said surgical drape.

18. In a surgical drape comprising a main sheet of flexible drapable material and retainer means for securing elongated elements such as suction tubing and electrical wires to said drapes, the improvement wherein said retainer means is made from a material selected from the group consisting of a woven fabric, a nonwoven fabric, a plastic film, and a liquid absorbent material laminated to a polymeric film and comprises an elongated, open-ended conduit through which said elongated elements may be threaded and thereby secured in desired position on said drape, said retainer means being attached to said sheet along a single line of attachment.

19. In a surgical drape comprising a main sheet of flexible drapable material, a fenestration, and retainer means for securing elongated elements such as suction tubing and electrical wires to said drape, the improvement wherein said retainer means is made from a material selected from the group consisting of a woven fabric, a nonwoven fabric, a plastic film, and a liquid absorbent material laminated to a polymeric film, comprising an elongated, open-ended conduit through which said elongated elements may be threaded and thereby secured in desired position on said drape, said retainer means being secured along a single line of attachment to said drape adjacent an edge of said fenestration, and said retainer means having a length which is substantially equal to the length of said edge.

20. A method for making a reinforced surgical drape comprising a main sheet; a reinforcing panel; and at least one retainer member comprising a conduit through which flexible elements such as suction tubing and electrical wires may be threaded to secure them to said drape, said method comprising:
   a. providing a main sheet of flexible drapable material having an upper surface, a lower surface, and a pair of opposed edges;
   b. providing a reinforcing panel of flexible, drapable material;
   c. forming at least one looped portion in said reinforcing panel, said looped portion being substantially parallel to an edge of said reinforcing panel and having a length substantially equal to the length of said edge of said reinforcing panel;
   d. securing said reinforcing panel with its said looped portion to the upper surface of said main sheet.

21. A method according to claim 20 wherein two said portions are formed in said reinforcing panel.

22. A method for making a fenestrated surgical drape comprising:
   a. providing a main sheet of flexible drapable material having an upper surface, a lower surface and a pair of opposed edges;
   b. cutting said sheet along first and second lines inwardly of said opposed edges;
   c. cutting said sheet along a third line joining said first and second lines to form at least one flap having an upper surface and a lower surface;
   d. folding said one flap so that one of said upper and lower surfaces of said flap comes into contact with itself; and
   e. securing said flap in said folded configuration.

23. A method according to claim 22 wherein said main sheet is further provided with a reinforcing panel.

24. A method according to claim 23 wherein said cutting is done through said reinforcing panel.

25. A method according to claim 24 wherein said first and second cuts are made generally parallel to each other.

26. A method according to claim 25 wherein said third cut is made generally perpendicular to said first and said second cuts.

27. A method according to claim 26 wherein said third cut substantially bisects said first and said second cuts.

28. A method for making a reinforced, fenestrated surgical drape, said drape having an upper surface, a lower surface, and at least one retainer member comprising a conduit through which flexible elements such as suction tubing and electrical wires may be threaded to secure them to said drape, said method comprising:
   a. providing a main sheet of flexible drapable material having an upper surface, a lower surface, and a pair of opposed edges;
   b. providing a reinforcing panel of flexible, drapable material;
   c. securing said reinforcing panel to the upper surface of said main sheet to form a reinforced main sheet;
   d. cutting said reinforced main sheet along first and second lines inward of said opposed edges, said first cut being generally parallel to said second cut;
   e. cutting said reinforced main sheet along a third line which joins and bisects said first and said second cuts to form first and second flaps, said first and second flaps each having an upper surface and a lower surface and being substantially equal in size;
   f. cutting through said reinforced main sheet along said first, said second, and said third lines;
   g. folding each of said flaps in half backwardly upon itself; and
   h. securing each of said flaps in its folded configuration.

* * * * *